United States Patent [19]

Djordjevic

[11] Patent Number: 5,023,172
[45] Date of Patent: Jun. 11, 1991

[54] PREDICTIVE ASSAY FOR TUMOR CONTROL

[75] Inventor: Bozidar Djordjevic, Astoria, N.Y.

[73] Assignee: The Research Foundation of State University of New York, Albany, N.Y.

[21] Appl. No.: 223,558

[22] Filed: Jul. 25, 1988

Related U.S. Application Data

[63] Continuation-in-part of Ser. No. 884,954, Jul. 14, 1986, abandoned.

[51] Int. Cl.$^5$ .................. C12Q 1/02; C12N 13/00; C12N 5/00; C12N 3/00
[52] U.S. Cl. .................. 435/29; 435/30; 435/32; 435/39; 435/173; 435/240.2; 435/240.22; 435/242; 435/243
[58] Field of Search .................. 435/29, 30, 39, 173, 435/240.1, 240.22, 242, 32, 240.2, 243

[56] References Cited

U.S. PATENT DOCUMENTS

| | | | |
|---|---|---|---|
| 4,225,486 | 9/1980 | Suzuki | 424/177 |
| 4,379,839 | 4/1983 | Spiegelman | 435/5 |
| 4,423,145 | 12/1983 | Stampfer et al. | 435/32 |

OTHER PUBLICATIONS

Djordjevic et al., "Clonogenicity of Mammaliam Cells in Hybrid Spheroids: a New Assay Method", (1989), pp. 1–16.
B. Djordjevic et al., "Potentiation of Radiation Effects in Hypoxic HeLa Cells", *Radiology*, 125, pp. 525–527 (1977).
Djordejevic et al., "Responses of Synchronous Populations of HeLa Cells to Ultraviolet Irradiation at Selected Stages of the Generation Cycle", *Radiation Res.*, 32, pp. 327–346 (1967).
R. Durand et al., "Effects of Intercellular Contact on Repair of Radiation Damage", *Exp. Cell Res.*, 71, pp. 75–80, (1972).
A. Hamburger et al., "Primary Bioassay of Human Tumor Stem Cells", *Science*, vol. 78, pp. 461–463 (1977).
K. Kal and G. Barendsen, "*In Vitro* Methods for Predicting Response", in *Cancer Treatment: End Point Evaluation*, pp. 321–338 (1983).
L. Peters et al., "Predictive Assays of Tumor Radiocurability", *Cancer Treatment Symposia*, 1, pp. 67–74 (1984).
N. Pourreau-Schneider et al., "Relationship Between Surviving Fractions Using the Colony Method, the LD50, and the Growth Delay After Irradiation of Human Melanoma Cells Grown as Multicellular Spheroids", *Radiation Res.*, 85, pp. 321–332 (1981).
M. Sapozink et al., "Effect of Hypoxia on Synchronous HeLa Cells Irradiated with Fast Neutrons", *Radiology*, 110, pp. 691–698, (1974).
R. Sutherland et al., "Growth of Multicell Spheroids in Tissue Culture as a Model of Nodular Carcinomas", *J. Mat'l Cancer Inst.*, 46, pp. 113–120 (1971).
R. Sutherland et al., "A Multi-Component Radiation Survival Curve Using an *In Vitro* Tumor Model", *Inst. J. Radiat. Biol.*, 18, pp. 491–495 (1970).
D. Von Hoff and L. Weisenthal, "*In Vitro* Methods to Predict for Patient Response to Chemotherapy", *Adv. Pharmacol, Chemother.*, 17, pp. 133–156 (1980).

(List continued on next page.)

*Primary Examiner*—Esther L. Kepplinger
*Assistant Examiner*—Florina B. Hoffer
*Attorney, Agent, or Firm*—Morgan & Finnegan

[57] ABSTRACT

An in vitro method for determining clonogenicity of and measuring the effect of physical (such as radiation or heat) or chemical treatment on mammalian test cells, including normal and tumor test cells. The method comprises encasing the test cells in agglomerates of non-proliferating, but metabolically active, feeder cells which are capable of forming spheroids. The resulting mixed (hybrid) multicellular spheroids provide an in vivo-like environment for the entrapped test cells. Test cells are subjected to treatment either before or after incorporation into spheroids, and the effect of such treatment is then evaluated from the colony forming ability of spheroids containing test cells.

31 Claims, 8 Drawing Sheets

OTHER PUBLICATIONS

J. Yuhas et al., "A Simplified Method for Production and Growth of Multicellular Tumor Spheroids", *Cancer Res.*, 37, pp. 3639–3642 (1977).

B. Djordjevic et al., "Oxygen Enhancement Ratios in HeLa Cells, Irradiated with Californium and Radium Sources", *Radiology*, 107, pp. 429–434 (1973).

B. Djordjevic, "Differential Effect of Procaine on Irradiated Mamalian Cells in Culture", *Radiology*, 131, pp. 515–519 (1979).

B. Djordjevic, "Modification of Radiation Response in HeLa Cells by Misonidazole", *Int. J. Radiat. Biol.*, 36, pp. 601–612 (1979).

B. Djordjevic, "Variable Interaction of Heat and Procane in Potentiation of Radiation Lethality in Mammalian Cells of Neoplastic Origin", *Int. J. Radiat. Biol.*, vol. 43, No. 4, pp. 399–409 (1983).

B. Djordjevic and J. Kim, "Modification of Radiation Response in Synchronized HeLa Cells by Metabolic Inhibitors: Effects of Inhibitors of DNA and Protein Synthesis", *Radiat. Res.*, 37, pp. 435–450 (1969).

J. Hendry et al., "The Gastrointestinal Syndrome and Mucosal Clonogenic Cells: Relationships Between Target Cell Sensitivities, $LD_{50}$ and Cell Survival, and Their Modification by Antiobiotics", *Radiation Res.*, 96, pp. 100–112 (1983).

S. Kim et al., "Enhancement of the Radiation Response of Cultured Tumor Cells by Chloroquine", *Cancer*, 32, pp. 536–540 (1973).

C. Lange, "Studies on the Cellular Basis of Radiation Lethality: I. The Pattern of Mortality in the Whole-Body Irradiated Planarian (Tricladida, Paludicola)", *Int. J. Radiat. Biol.*, 13, pp. 511–530 (1968).

C. Lange, "Studies on the Cellular Basis of Radiation Lethality: II. Survival–Curve Parameters for Standardized Planarian Polulations", *Int. J. Radiat. Biol.*, 14, pp. 119–132 (1968).

C. Lange, and W. Gilbert, "Studies on the Cellular Basis of Radiation Lethality: III, The Measurement of Stem-Cell Repopulation Probability", *Int. J. Radia. Biol.*, 14, pp. 373–388 (1968).

C. Lange, "Studies on the Cellular Basis of Radiation Lethality: IV, Confirmation of the Validity of the Model and the Effects of Dose Fractionation", *Int. J. Radiat.*, 14, pp. 539–551 (1968).

C. Lange, "Studies on the Cellular Basis of Radiation Lethality: V, A Survival Curve for the Reproductive Integrity of the Planarian Neoblast and the Effect of Polyploidy on the Radiation Response", *Int. J. Radiat. Biol.*, 15, pp. 51–64 (1968).

T. Munro and C. Gilbert, "The Relation Between Tumour Lethal Doses and the Radiosensitivity of Tumour Cells", *British J. Radiat.*, XXXIV, pp. 246–251 (1961).

E. Sakiyama et al., "Effects of Confluent Monolayers of Density-Inhibited and Transformed Cells on the Growth of Superinoculated Cells", *Cancer Res.*, 38, pp. 2854–2858 (1978).

S. Silagi et al., "Suppression of Malignancy and Differentiation in Melanotic Melanoma Cells", *Proc. Nat'l Acad. Sci.*, 66, pp. 72–78 (1970).

C. Wallen, "Comparison of the Cell Kill Measured by the Hoechstpropidium Iodide, Flow Cyteometirc Assay and the Colony Formation Assay", *Cell Tissue Kinet.*, 16, pp. 357–365 (1983).

P. J. Tofilon et al., "Effect of Cell-Cell Interactions on Drug Sensitivity and Growth of Drug-Sensitive and -Resistant Tumor Cells in Spheroids", *Science*, 226, pp. 862–864 (1984).

H. Gershman et al., "Sorting Out of Normal and Virus-Transformed Cells in Cellular Aggregates", *J. Cell. Biol.*, 68, pp. 276–286 (1976).

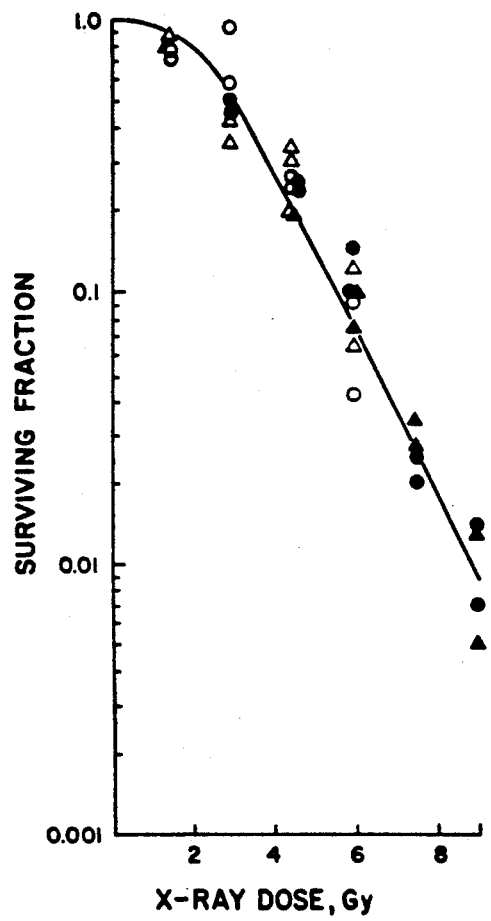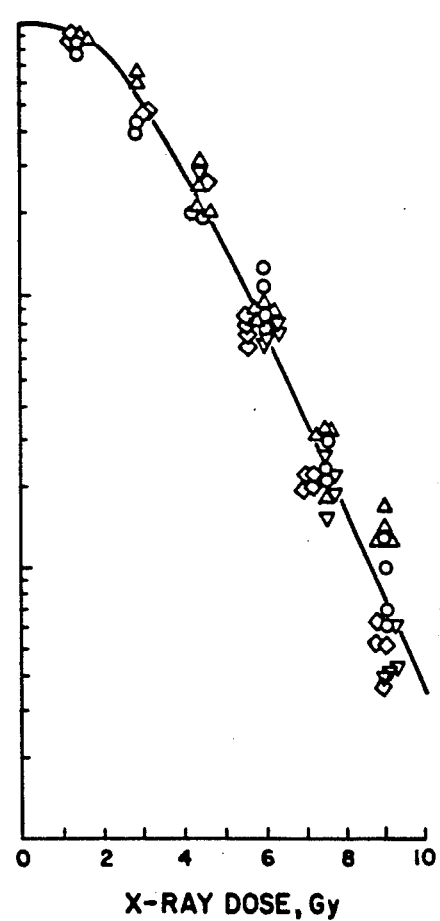
Fig. 3A.
Fig. 3B.

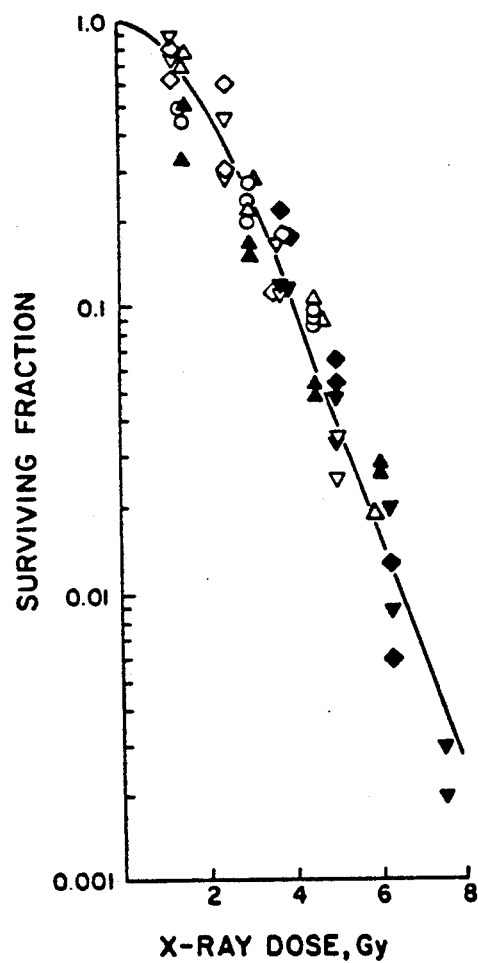 _Fig.5A._
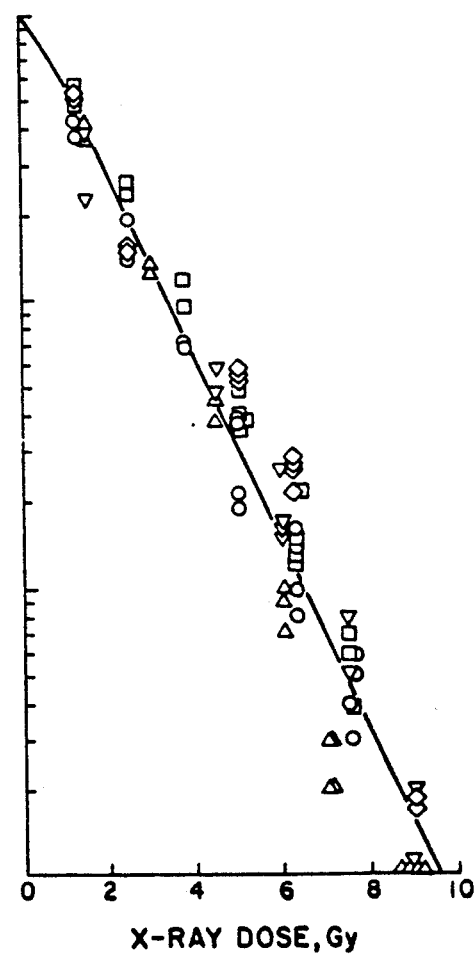 _Fig.5B._

PREDICTIVE ASSAY FOR TUMOR CONTROL

The invention described herein was supported by a grant awarded by the National Institutes of Health No. RO1 CA 35289.

This application is a continuation-in-part of Application Serial No. 06/884,954, filed July 14, 1986, now abandoned and which is incorporated herein by reference.

BACKGROUND OF THE INVENTION

There is a need for a reliable in vitro tumor model system for testing the effect of chemical or physical (such as radiation or heat) treatment on tumor cells and the effect of such treatment on surrounding normal cells, which would accurately reflect the effect of such treatment on an actual in vivo tumor. At present, soft agar stem cell techniques are known as in vitro tumor assay methods. See A.W. Hamburger et al., "Direct Cloning of Human Ovarian Carcinoma Cells in Agar," 38 *CAncer Res.* 3438-3447 (1978). However, soft agar assay methods have several limitations and drawbacks: (a) not all tumor biopsy samples yield colonies which are suitable for soft agar assays; (b) the plating efficiency of this system is very low (ca $10^{-5}$) and appears not to be typical of in vivo tumor clonogens; and (c) the system is not suitable for radiation studies. In addition, the systems predictive ability is also limited.

Attempts have also been made to use multicellular tumor spheroids (MTS) systems for assaying tumor inactivating agents. See, J.M. Yuhas et al., "In Vitro Analysis of the Response of Multicellular Tumor Spheroids Exposed to Chemotherapeutic Agents in Vitro or in Vivo," 38 *Cancer Res.* 3595-3598 (1978).

MTS systems are desirable as in vitro models because some of their features more closely resemble those of actual in vivo tumors than those of the soft agar techniques. See R.M. Sutherland, "Cell and Environment Interaction in Tumor Microregions: The Multicell Spheroid Model." 240 *Science,* 177-184 (1988); R.E. Durand, "Cure, Regression and Cell Survival: A Comparison of Common Radiobiological Endpoints Using an in Vitro Tumor Model," 48 *British Journal of Radiology,* 556-571 (1975). For example, often in both spheroids and in tumors there is an increased survival rate for the cells when they are maintained in close contact during and after radiation treatment. The differences in survival rates of cells in spheroids are attributed to several factors, including hypoxia in spheroids as well as the three-dimensionality of cellular contact within these bodies. See, R.P. Hill et al., "The Effect of Intercellular Contact on the Radiation Sensitivity of KHT Sarcoma Cells," 77 *Radiation Res* 182-192 (1979); G.M. Hahn et al., "Repair of Potentially Lethal Damage in Vivo in Solid Tumor Cells After X-radiation,"34 *Cancer Res.* 351-354 (1974); R.E. Durand and R M. Sutherland, "Effects of Intercellular Contact on Repair of Radiation Damage," 71 *Exp. Cell Res.* 75-80 (1972); H. Gershman, J. Drumm and L. Culp, "Sorting of Normal and Virus-Transformed Cells in Cellular Aggregates," 68 *Journal of Cell Biology,* 276-286 (1976); P.J. Tofilon, N. Buckley and D.F. Deen, "Effect of Cell-Cell Interactions on Drug Sensitivity and Growth of Drug-Sensitive and Resistant Tumor Cells in Spheroids," 226 *Science* 862-864 (1981).

The use of presently available MTS assay systems however, cannot be applied to all test cells, such as tumor cells, because not all test cells are capable of forming spheroids. For example, A.C. Jones et al., "In Vitro Cytotoxic Drug Sensitivity Testing of Human Tumor Xenografts Grown as Multicellular Tumor Spheroids," 46 *Br. J. Cancer* 870-879 (1982), report that none of the cells taken directly from tumors of seven patients could form spheroids, while only 5 out of 22 cell lines grown as xenografts could do so. Thus, at present, use of MTS systems for the study of tumor inactivating agents is restricted to those cells which are capable of forming spheroids. In addition, because the present MTS assay system is tailored to the particular test cell type which comprises the MTS system, MTS studies are not conducted under uniform conditions and, thus, do not yield uniform, comparable results.

DEFINITIONS

As used herein, the following terms have the indicated meanings:

agglomerate: A tightly packed group of cells formed by the clumping together of formerly dissociated cells. The agglomerate may contain entrapped therein non-agglutinating cells.

clonogen: Also known as a "stem cell." A single cell capable of giving rise to many progeny, a clone.

feeder cells: Cells which are capable of agglomerating and forming spheroids, but are not capable of proliferation.

mixed (or hybrid) spheroids: Cell agglomerates of heterogeneous origin having rounded appearance.

mammalian test cells: Those cells, such as normal and tumor cells and their progeny, including but not limited to mutants thereof, whose clonogenicity and survival rate is being investigated. Reference to test cells in the text should be understood to mean mammalian test cells and their progeny, including but not limited to mutants thereof, unless otherwise specified.

SUMMARY OF INVENTION

This invention provides a new in vitro method for determining the clonogenicity of, and measuring the effect of various treatments, such as physical (e.g. radiation or heat) or chemical treatments, or a combination thereof, on mammalian test cells and their progeny, including but not limited to mutants thereof, particular human normal and tumor cells and their progeny, including but not limited to mutants thereof, by the use of the novel hybrid multicellular spheroid systems.

In these hybrid multicellular spheroid systems, clonogenic mammalian tumor test cells are packaged into manageable cell agglomerates so as to simulate in vivo tumor systems. According to the invention, these in vitro "mini-tumors" are formed by encasing or entrapping the test cells, for example tumor stem cells, in agglomerates of non-proliferating but metabolically active feeder cells, for example HeLa cells, which are capable of forming spheroids of uniform size and which serve to provide a simulated in vivo environment.

Clonogenicity of the hybrid spheroids is then determined. For example, clonogenicity may be determined by application of statistical analysis methods appropriate for the evaluation of random events In one such method used by the Applicant, clonogenicity of the test cells is determined by varying the ratio of test to feeder cells in the combined cell suspension from which spheroids are formed so that some, but not all, spheroids give rise to macrocolonies. From the fraction of non-colony forming spheroids, the average number of clonogens per spheroid can be calculated, and the clonogenicity of the test cells determined by solving for the zero term of the poisson distribution function. The method and appropriate corrections for special cases is developed fully in Examples 1 and 2. Because selected spheroids of uniform size are used in the procedure to be described, clonogenicity of the test cells can be easily quantified without resorting to dispersive techniques. This is an advantage over the previously used more cumbersome and expensive methods such as xenograft assays in nude mice or presently available dispersive techniques. In addition, cells which do not grow as single cells after dispersion, often do grow in these mixed spheroid systems.

The test-cell-containing spheroids of the present invention, which will be termed hybrid spheroids, can then be subjected to a desired form of treatment, such as chemical or radiation treatment or combinations thereof, and the survival rate of the treated test cells in the hybrid spheroids determined. Alternatively test cells can be treated prior to incorporation into spheroids, when such mode of treatment is advisable, and their survival in hybrid spheroids measured.

It should be emphasized that the new method is easy to apply and simple to interpret. For most cases (those involving tumor cells), the effect of treatment (radiative, chemical or combinations thereof) is obtained by relating clonogenicities without resorting to complicated corrections, such as cell multiplicity factors. The latter are nevertheless described in detail in the Examples to demonstrate the breadth and wide applicability of the Method to various cell types and treatment protocols.

Thus, the present invention provides a novel in vitro predictive tumor and normal cell control assay which embodies the methodology of preparing hybrid spheroids (including the mode of preparation and inactivation of the agglomerating feeder cells), the statistical analysis used to measure clonogenicity (as well as various corrections required for special cases) and the methodology necessary for exposing the hybrid spheroids to radiative or chemical regimens or combinations thereof being assayed for their efficacy in therapeutic interventions. Some of the advantages of the novel method described herein are: (a) the method is suitable for various test cells, test cell lines or test cells obtained directly from mammalian tumors; (b) it accurately predicts the effect of several forms of treatment on in vivo tumor clonogens without complicated assessment techniques; (c) it may be employed with test cells which do not themselves form agglomerates; (d) it yields spheroids which are metabolically active for an extended period of time (currently 5-10 days), and (e) it increases the plating efficiency of cultured mammalian tumor cells, which normally plate rather poorly, when incorporated into hybrid spheroids.

This novel method is anticipated to be particularly useful in tailoring chemotherapeutic and/or radiative regimens to individual patients and to test new treatment protocols and agents.

BRIEF DESCRIPTION OF THE DRAWINGS

FIGS. 3A-B: FIG. 3A is an X-ray survival curve for B-16 cells irradiated in hybrid spheroids. FIG. 3B is an X-ray survival curve for B-16 cells irradiated immediately after plating as monodispersed cells. Full symbols denote an increased input of test cells to offset decreased survival with dose, in the same manner as described for HeLa cells. Survival curve parameters FIG. 3A: $D_0=1.40\pm0.06$ Gy, n=5.9 (95% FL, 4.0–8.7); survival curve parameters FIG. 3B: $D_0=1.31\pm0.06$ Gy, n=7.7 (95% FL, 4.7–12.7).

FIG. 4A depicts a spheroid stained 1.5 h after plating. FIG. 4B depicts a colony developed from an encircled 1:100 test:feeder hybrid spheroid after 11 days of incubation. FIG. 4C depicts remnants of an encircled spheroid lacking clonogens, detected on the same flask as the colony in FIG. 4B. FIG. 4D depicts remnants of an encircled 1:20 hybrid spheroid which had been irradiated with 3.75 Gy and incubated for 11 days.

FIGS. 5A-B: Show X-ray survival curves for HeLa cells corrected for cellular multiplicity. FIG. 5A depicts cells irradiated in spheroids. FIG. 5B depicts cells irradiated in monolayer. Differently shaped symbols are from different experiments, with solid symbols denoting an increased input of test cells, as explained in the test. Survival curve parameters FIG. 5A: $D_0=1.10\pm0.05$ Gy, n=3.8 (95% FL, 2.6–5.4); FIG. 5B: $D_0=1.33\pm0.03$ Gy, n=1.3 (95% FL, 1.1–1.6).

FIG. 6A is an X-ray survival curve for HeLa cells irradiated and then incorporated into spheroids. FIG. 6B is an X-ray survival curve for HeLa cells irradiated immediately after plating. Circles in FIG. 6A denote an experiment with an increased input of test cells with dose to offset decreased survival. Triangles denote 1:100 hybrid spheroids. Survival curve parameters FIG. 6A: $D_0=1.22\pm0.09$ Gy, n=2.3 (95% FL, 1.4–3.8); survival curve parameters FIG. 6B: $D_0=0.99\pm0.04$ Gy, n=5.2 (95% FL, 3.0–9.0).

FIGS. 7A-F: Show growth characteristics of HEp3 cells after 14 days of incubation. FIG. 7A shows a typical area of a flask seeded with $1.5 \times 10^4$ cells which contains an estimated number of 360 denser groupings of cells (not readily scorable as colonies). FIG. 7B shows an encircled 1:5 HEp3-HeLa feeder hybrid spheroid which had developed into a colony. FIG. 7C shows a similar encircled spheroid which had failed to produce a colony. FIGS. 7D-F are the same as FIGS. 7A-C but for cells of spheroids irradiated with 4 Gy. Magnification is 24x.

DETAILED DESCRIPTION OF THE INVENTION

Figure 1:
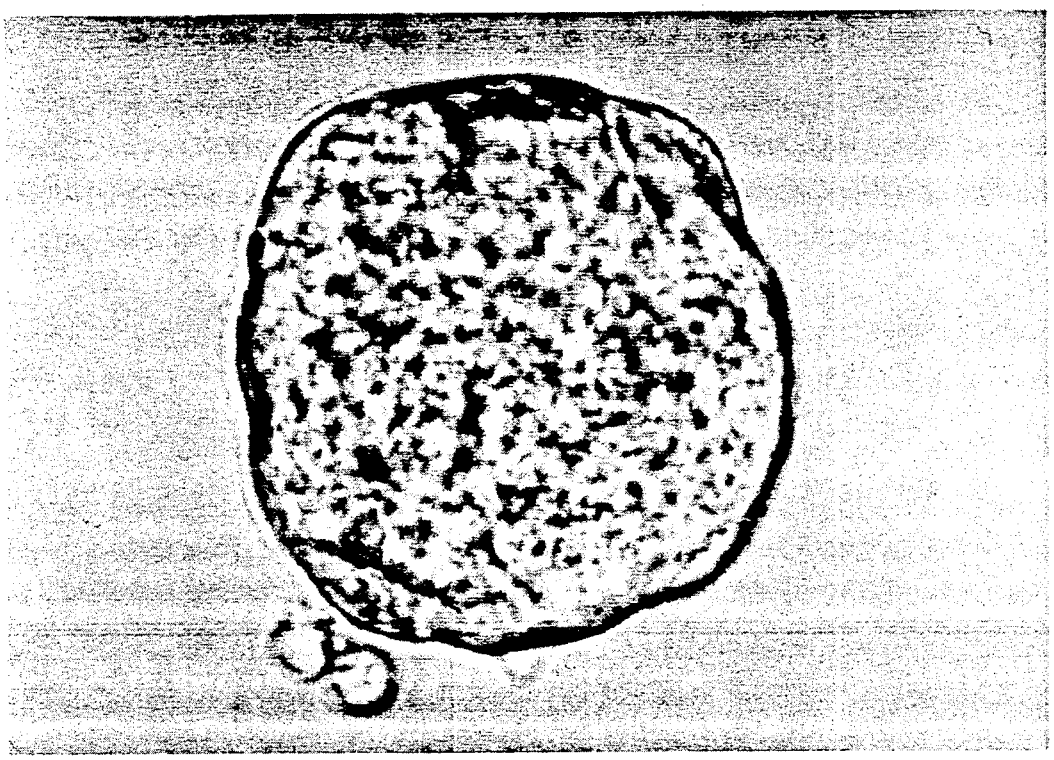
FIG. 1: Depicts a multicellular spheroid formed from clonogenically inactivated HeLa cells after 20 hours incubation at 37° C. The magnification is 1000 x.

This invention is directed to a novel method of conducting a predictive in vitro assay for determining the clonogenicity of mammalian test cells and their progeny, including but not limited to mutants thereof, particularly human test cells and their progeny, including but not limited to mutants thereof, more particularly, human tumor and normal test cells and their progeny, including but not limited to mutants thereof, and for selecting effective treatment protocols that can be tailored to each patient afflicted with any of a variety of different tumors. According to this method, the cells under study, e.g., tumor stem cells, are encased or entrapped in agglomerates of non-proliferating, that is, clonogenically inactive, but metabolically active, "feeder" cells. The resulting in vitro "mini-tumors" provide a simulated in vivo environment that allows for effective study of protocols for treatment of patients afflicted with tumors of the test-cell type.

Inactivation of Feeder Cells

The feeder cells useful in this method include those cells which are capable of agglomerating when cultured at high density, for example, HeLa and V79 Chinese hamster cells. Preferred feeder cell types are HeLa-S3 cell lines, such as the HeLa S-3 SKI cell line.

Feeder cells may be rendered capable of agglomerating by treating with inactivated virus (for example, Sendai virus), ethylene glycol or MEM supplemented with fetal calf serum. Preferably, the feeder cells are grown in MEM (with or without DL serine) supplemented with fetal calf serum and antibiotics. If the MEM does not contain DL serine, it may be optionally added. Feeder cells may be clonogenically inactivated by chemical or radiation treatment or a combination of both. Preferred methods of inactivation of feeder cells, particularly for HeLa feeder cells, include incubation with bromodeoxyuridine (BUdR) and flurodeoxyuridine (FUdR), illumination with visible light, X-irradiation, and/or a combination of these treatments. Inactivation by treatment with BUdR and FUdR is preferably effected by incubation for about 1 to 3 days, most preferably three (3) days, with from about $10^{-6}$ M BUdR to $10^{-4}$ M BUdR, preferably from $10^{-5}$ M BUdR to $5 \times 10^{-5}$ M BUdR, and more preferably $2 \times 10^{-5}$ M BUdR and from about $10^{10}$ M to $10^{-7}$ M FUdR, preferably $1.5 \times 10^{-8}$ M FUdR.

Inactivation is also advantageously effected by irradiating the feeder cells with X-rays, preferably at doses of from about 7.5 Gy to about 30 Gy, most preferably 10 Gy.

Most preferred inactivation of feeder cells is effected by incubation for three (3) days in the presence of $2 \times 10^{-5}$ M BUdR and $1.5 \times 10^{-8}$ M FUdR followed by irradiation with 10 Gy of X-rays. Alternatively to x-irradiation, the cells may be illuminated under a 15 watt fluorescent desk lamp, at a distance of about 7.5 cm for about 20-minutes to achieve feeder cell inactivation.

When irradiating the feeder cells, it is important to avoid excessive doses of radiation and/or visible light, inasmuch as this adversely affects the ability of these cells to agglomerate and may thus prevent spheroid formation.

Preparation of Single Test Cell Suspensions

Test cell suspensions from established cell lines and normal cells are prepared by methods known to those skilled in the art. See, e.g., R.E. Durand and R.M. Sutherland, "Effects Of Intercellular Contacts On Repair Of Radiation Damage," 71 *Exp. Cell. Res.* 75-80 (1972)

Test cell suspensions derived directly from surgical specimens from mammalian or human tumors may be prepared following the method of Arundel. See C. Arundel, S. Bock, W.A. Brock and P.J. Tofilon, "Radiosensitization of Primary Human Cell Cultures by N-methylformamide," 13 *International Journal of Radiation Oncoloqy, Biology Physics,* 753-757 (1987).

Briefly, tumor specimens are washed in phosphate buffered saline and about 0.5-5 gm (preferably 1 gm) of the specimen is minced with crossed scalpels in a bacteriological petri dish. The minced tissue is then transferred into a 125 ml Erlenmeyer flask containing 15-80 ml (preferably 20 ml) of an enzyme cocktail of collagenase (preferably type IV, 0.01-0.5%, preferably 0.075%) and 0.05-0.0005%, preferably 0.005% of DNase (both from Sigma Chemical Company, St. Louis, MO) in RPMI-1640 medium with HEPES buffer (pH 7.3±0.1) and supplemented with 10% fetal calf serum (both from GIBCO). After overnight incubation at 37° C. with constant stirring, the enzyme digest is passed through a 37 micrometer (um) sieve, the cell suspension washed and the cells dispersed in RPMI-1640 medium containing 20% fetal calf serum. The dispersed cells are then stained with trypan blue and the viable cells counted. The test cell suspension is then ready for hybrid spheroid formation.

Preparation Of Hybrid Spheroids

Clonogenically inactivated feeder cells are prepared by one of the methods described above. Non-confluent monolayers are irradiated with 10 Gy of x-rays, trypsinized and $3-5 \times 10^6$ cells adjusted to a volume of 5 ml in MEM. Such cells are non-proliferating and, at the same time, highly agglutinable. They also retain their metabolic viability while assembled in agglomerates. Concurrently, non-confluent HeLa, B-16, HEp3 test cells, normal human cells or human tumor cells obtained directly from a surgical specimen (see Table I, Example 1), are trypsinized, diluted in MEM, and a desired number added in a volume of 1-5 ml MEM on RPMI-H40 medium to the feeder cell suspension. The vortexed combined cell suspension is sedimented at low speed, and the pellet incubated 0.5-2 ml, preferably 1 ml MEM for 1.5 hours at 37° C. An additional 5-15 ml, preferably 9 ml of MEM is added to the cells, and the suspension transferred into a 100 mm bacteriological petri dish; this procedure is aimed at encouraging cell agglomeration, similar to that described by Yuhas (1977). After overnight incubation at 37° C. in the 5% $CO_2$ incubator, a large number of rounded cell agglomerates form in the petri dish. These bodies are of various sizes and tend to attach to each other upon manipulating the petri dish. Rounded agglomerates are termed hybrid spheroids, to denote their heterogeneous origin and rounded appearance.

A homogenous population of spheroids is obtained by passing the contents of the petri dish through a series of nylon sieves (also termed micrometer filters and obtained from Small Parts Inc., Miami, FL). In the majority of experiments where established cell lines are used as test cells, hybrid spheroids which pass a 105 micrometer nylon pore sieve and are retained on a 88 micrometer pore sieve are used. Other size spheroids (88-149 micrometer) are also selected when this was deemed necessary, as with spheroids containing test cells isolated directly from tumor specimens. In these cases, spheroids passing through 149, 125 or 105 micrometer pore filters are harvested by rinsing the spheroids retained on the next smaller size micrometer pore sieves in 12 ml MEM or RPMI-1640 medium (the latter for spheroids containing tumor cells). The method is anticipated to be applicable to spheroids ranging in size from 85-170 micrometers. FIG. 1 illustrates a typical spheroid.

To follow the fate of spheroids containing test cells, one of the following procedures is employed: (a) hybrid spheroids are picked individually from a suspension and placed into separate wells of 24 or 96 well tissue culture plates as outlined in Example 1; (b) spheroids are allowed to attach to the growth surface of culture vessels where their position is marked; or (c) an average of 5 spheroids is plated per well of 24 well plates, where their position after attachment is recorded on a film (negatives suffice for this purpose). Method (b) is preferred for mass-screening of spheroids and is described below.

A series of 30 ml tissue culture flasks is inoculated with no more than 200 spheroids per flask in appropriate medium (MEM or RPMI-1640 supplemented with 20% of fetal calf serum, the latter used for spheroids containing cells isolated directly from tumors), and the spheroids allowed to attach to the growth surface of the flask. After a 1.5-2 hour incubation period at 37° C., the position of well-isolated surface-attached spheroids is marked on the flask bottom. For this purpose, flasks are sealed and inspected in inverted position under a dissecting microscope for brief periods of time. Flasks with marked positions of spheroids are returned to the incubator and held there, for a period of 10-14 days (14 days for spheroids containing cells isolated from tumor specimens), to allow colony formation. All colonies are stained with crystal violet, and inspected under the dissecting microscope. Colony counts are based only on colonies larger than expected from an assembly of abortive micro-colonies when flasks are inoculated with spheroids, or on colonies larger than 50 cells in the case of conventionally plated cells (used for comparison with test cells grown from spheroids). Survival curves of conventionally irradiated cells are fitted to the single-hit, multi-target model, fitted by nonlinear least squares using the SYSTAT program. This program minimizes first by the Simplex method (R. O'Neil, 47 "Function Minimization Using a Simplex Procedure Algorithm," 388–400 (1971); P. Griffiths and I.D. Hill, *Applied Statistics Algorithms,* Chichester: Ellis Harwood, 1985), followed by a re-estimation with Quasi-Newton minimization. (R. Fletcher, *Fortran Subroutines for Minimization by Quasi-Newton Methods* p. 7125 (1972).

Occasionally a more laborious procedure to follow the fate of plated spheroids is used. In this procedure individual spheroids are picked with a pasteur pipette under a dissecting microscope and placed in individual wells of 96 well plates. After filling the wells, each is inspected under the microscope and those without a spheroid or with multiple spheroid occupancy noted. Afterwards, staining and scoring of colonies is identical as in the case when spheroids were plated into flasks.

Clonogenicity Assay

If only a fraction of spheroids form colonies, clonogenicity (clones per spheroid) can be readily determined. If more than 90% of spheroids form colonies, spheroid formation should be repeated with a smaller proportion of test to feeder cells and colony forming ability measured again. Clonogenicity is most accurately measured in the 30-70% range of colony-forming spheroids (where a random distribution of test cells in spheroids can be reasonably assumed), and is deduced from the non-colony forming spheroids explicitly using the zero-term of the poisson distribution as is described in Example 1. Thus, one obtains the number of clones per spheroid in a particular preparation.

Radiotherapeutic Treatment of Hybrid Spheroids

Hybrid spheroids are irradiated after attachment to the growth surface of 30 ml tissue culture flasks, after the position of individual spheroids was marked as outlined above. After irradiation, flasks are returned to the 37° C. incubator for colony formation.

Test cells could also be irradiated first, and then incorporated into spheroids, as described in Examples 1 and 2. Their viability is assayed as described above.

Chemical Treatment of Hybrid Spheroids

For chemotherapeutic treatment, about 10 ml of a suspension of spheroids of different sizes is transferred into 10 cm bacteriological dishes (where attachment is discouraged) and incubated with a given chemotherapeutic agent, drug or chemical supplement for a desired period of time (usually 2-5 hours, preferably 3 hours). The range of concentrations of the chemotherapeutic agent, drug or chemical being investigated should cover that found in the blood plasma of patients undergoing clinical trials or, where this information is not available, the concentration ranges should be broad enough to include anticipated plasma concentrations. These chemotherapeutic agents, chemicals or drugs could include, for example, Adriamycin, doxorubicin hydrochloride, cyclophosphamide, cis-platinum, 5-fluorouracil, methotrexate, vinblastine sulfate, melphalan and vincristine sulfate.

After the treatment period, spheroids are washed by pouring the suspension over sieves (mounted on a sterile tea strainer) of a pore size smaller than the spheroids and rinsing the retained spheroids with phosphate-buffered saline to remove traces of the chemotherapeutic agents, drugs or chemicals. After washing, spheroids are harvested as described above and plated for clonogenicity measurements.

Determination Of Cell Survival After Treatment

To calculate survival of test cells entrapped in spheroids, their clonogenicities before and after treatment are determined. Clonogenicity may be measured using a poisson distribution as illustrated in Example 1. For example, if one obtains from the zero-term of the poisson distribution of colony formers among spheroids, an average of 1.2 clonogens per spheroid in the untreated series, and an average number of 0.36 clonogens per spheroid in the treated series, the survival would then be calculated to be 0.36/1.2=0.3, i.e. 30% of control. That is, that particular form of treatment results in 70% killing of the initial cell population. For lower survival values, a larger input of test cells into spheroids is necessary to obtain a usable ratio of colony formers to non-formers among the spheroids. This increased input of test cells into spheroids of the treated series is then reflected in survival calculation in a simple arithmetical procedure as is also outlined in Example 1.

In a simple case, as illustrated by the above example, a random distribution of cells in a spheroid is assumed, hence the use of the poisson distribution is justified. However, when test cells proliferate within spheroids before irradiation, the distribution of cells among spheroids is no longer random, and an appropriate corrective factor has to be introduced in calculating survival. This so called "cell multiplicity" factor enables survival to be related to single-clonogen colony-forming units, such that inactivation of every clonogen will be seen after treatment. The procedure for multiplicity correction of survival of clonogens in spheroids is outlined in Example 2.

It should be noted that no multiplicity corrections are needed when test cells are irradiated before incorporation into spheroids, or when there is no proliferation of test cells after their incorporation into these bodies and before radiation or other treatment. Thus, when the intrinsic value of the true cellular survival is desired and the cellular multiplicity is difficult or impossible to obtain, parallel series of cells are treated with graded doses and only then incorporated into spheroids. On the other hand, when it is important to treat whole spheroids, and cellular multiplicity. is easy or unimportant to determine, the former procedure may be preferred. As a rule of thumb, for all preliminary findings, treatment of whole spheroids (a simpler procedure, where fewer preparations have to be made) is performed, followed by the more precise measurement of true cellular survival. There is little difference between the two procedures when cell proliferation in spheroids is slow.

The following Examples present illustrative, but non-limiting, embodiments of the present invention. Particular attention is given in Example 1 to developing the statistical treatments necessary to obtain meaningful determinations of clonogenicities. Example 2 demonstrates the validity of the hybrid spheroid method for clonogenicity measurements by comparing it directly to cells assayed by a conventional clonogenicity method. Example 3 demonstrates that the method passes the ultimate test for novelty, namely, the method is shown to be superior to conventional plating methods for those test cell types which exhibit poor plating characteristics.

EXAMPLE 1

Cell Lines And Maintenance

Both established cell lines, normal mammalian cells and mammalian tumor cells (derived directly from a wide variety of mammalian and human tumors) can be used to form hybrid spheroids (see Table I listing the types of human tumor cells used and their organ of origin). In this Example, HeLa S-3 cells were used as feeder cells and mouse melanoma B-16 cells were used as test cells. Cells were grown in MEM supplemented with 10% fetal calf serum (GIBCO), 84 mg/L DL serine, and antibiotics. Plating efficiencies were 65% for HeLa cells and 75% for B-16 cells. Cultures were maintained in a humidified atmosphere of 5% CO, in air at 37° C., and subcultured twice weekly.

Preparation Of Hybrid Spheroids

To prepare clonogenically inactivated feeder cells, HeLa cells were grown for three (3) days in the presence of $10^{-5}$ M BUdR and $1.5 \times 10^{-8}$ M FUdR. Nonconfluent monolayers of cells were irradiated with 10 Gy of X-rays, and $3-5 \times 10^6$ cells were adjusted to a volume of 5 ml MEM. Concurrently, non-confluent B-16 test cells, were also irradiated at this stage with graded doses of X-rays. The irradiated B-16 cells were then trypsinized according to standard tissue culture procedures, diluted in MEM, and added, in a volume of 2-5 ml MEM, to the feeder cell suspension.

The vortexed combined cell suspension was sedimented at low speed, and the pellet incubated in 1 ml MEM for 1.5 hours at 37° C. Thereafter, an additional 9 ml of MEM was added to the cells, and the suspension transferred into a 100 mm bacteriological petri dish so as to encourage cell agglomeration as described by J.M. Yuhas et al., "A Simplified Method for Production and Growth of Multicellular Tumor Spheroids", 37 *Cancer Res.* 3639-3643 (1977).

After overnight incubation at 37° C. in a 5% $CO_2$ incubator, a large number of rounded cell agglomerates formed in the petri dish. These bodies were of various sizes and tended to attach to each other upon manipulation of the petri dish. A homogenous population of spheroids was obtained by passing the contents of the petri dish through a 105 micrometer nylon mesh filter (Small Parts, Inc., Miami, Fla.) and harvesting spheroids retained on the 88 micrometer filter. FIG. 1 demonstrates a typical selected spheroid.

Harvesting was accomplished by rinsing the 88 micrometer pore filter in 12 ml MEM. The total harvest was divided between a 60 mm tissue culture dish and a 100 mm bacteriological dish. The contents of the 100 mm bacteriological dish were used to maintain a supply of unattached spheroids. After a 30 minute period, spheroids in the tissue culture dish attached themselves to the bottom but remained rounded and suitable for individual selection with a pasteur pipette for a period of two (2) hours. For longer periods of selection, it is recommended that the procedure be repeated using the spheroids from the other (bacteriological) petri dish.

Spheroids of about 100 micrometers in diameter were then transferred under a dissecting microscope into individual wells of 24 or 96 well tissue culture plates. Each well was checked for occupancy, and empty wells and wells with more than one spheroid noted. Inoculated plates were incubated at 37° C. for ten (10) days before staining with crystal violet. Only colonies larger than expected from an assembly of abortive micro-colonies were counted.

Clonogenicity Assay Of The B-16 Test Cells In The Hybrid Spheroids

The number of clonogens per spheroid was determined based on the frequency of colony formation in undispersed spheroids, as is described below. In this analysis, a random distribution of test cells among spheroids is assumed. When only a fraction of spheroids form colonies (preferably in the 30-70% range), it is possible to deduce the average number of clonogens per spheroid by using the zero term of the Poisson distribution function. Thus, the number of clonogens per spheroid (cl) is obtained as follows:

$$1-(colonies/spheroid) e^{-cl} \text{ tm (1)}$$

$$cl = -\ln(1-(colonies/spheroid)) \qquad (2)$$

Because cl will vary with the input of test cells into spheroids, i.e. when the ratio of test to feeder cells in the initial suspension from which spheroids are formed, is varied, the value cl has to be normalized to a certain ratio of test to feeder cells. In this example, this value was 1:100. When normalizing cl values to standard spheroids, a factor derived from the ratio of the total number to the number of test cells in the actual and the normalized cell suspension is used. The following is a numerical expression of this correction:

$$cl \text{ (normalized to 1:100 spheroids)} = \qquad (3)$$

$$\frac{cl \text{ (observed)} \times \text{(total/test cells in suspension)}}{101}$$

It is the total number of cells, rather than the number of feeder cells, that should be used in the above equation. For example, 41 would be used in the numerator for a 1:40 suspension.

Irradiation Technique And Evaluation Of Test Cell Survival In Hybrid B-16/HeLa S-3 Spheroids Both HeLa S-3 and B-16 cells were irradiated as monolayers with 250 kVp X-rays from a Philips 250 RT machine (HvL 0.39 mm Cu). Survival of irradiated B-16 cells in spheroids was determined from the ratio of clonogens per spheroids (cl) in the irradiated series, to that ratio in the pooled unirradiated series, multiplied by a factor. This factor corrects for the higher cellular occupancy (test cells per spheroid) introduced to compensate for killing of test cells by radiation, and is obtained in a similar fashion as the normalization factor used for spheroids with unirradiated test cells. It has 101 in the denominator, and a number corresponding to the ratio of total to test cells in the initial suspension of the irradiated series, in the numerator.

Fractional survival (S.F.) of irradiated test cells is thus expressed:

$$S.F. = \frac{cl \times \text{(total cells/test cells in suspension (irrad. series))}}{cl \times 101 \text{ (pooled control series)}} \quad (4)$$

Figure 2:
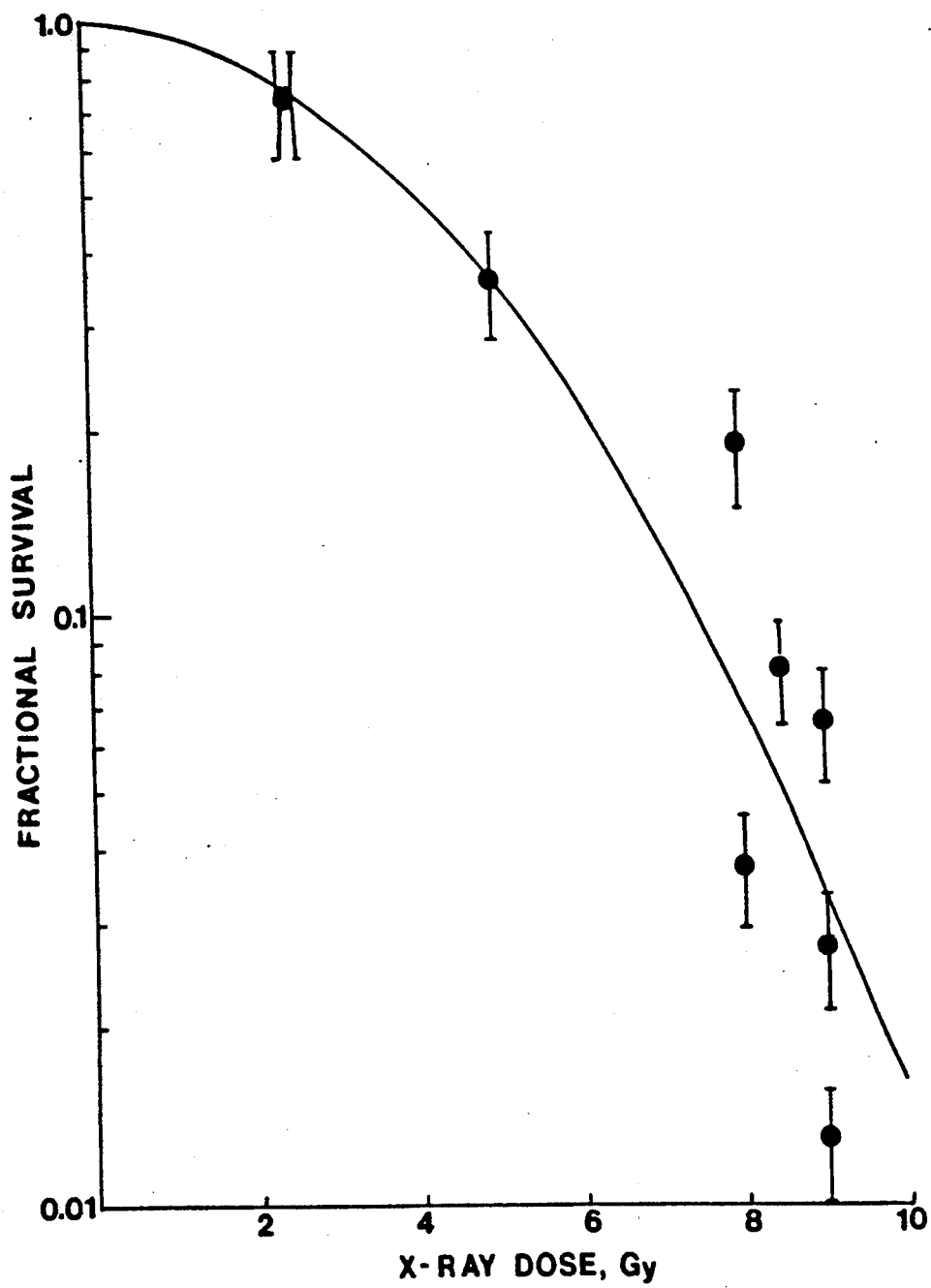
FIG. 2: Is a survival curve for B-16 cells irradiated and then assayed by the spheroid method, fitted to the linear-quadratic model of cell inactivation. Alpha $=0$; Beta $=4.13 \times 10^{-2}$ $(Gy^{-2})$.

The results of the fractional survival value calculations for B-16 cells subjected to varying doses of irradiation are reported in Table II. The data reported are based on the number of colonies obtained from a given spheroids (usually 96; i.e. seeded in a 96 well plate). After plotting data points recorded in Table II for all irradiated doses, a survival curve was fitted using the linear-quadratic model for cell inactivation as described by B. Fertil et al., "Mean Inactivation Dose: A Useful Concept for Intercomparison of Human Cell Survival Curves," 99 *Radiat. Res.* 73–84 (1984). The fractional survival curve is depicted in FIG. 2. As is evident from FIG. 2, test cells have a high survival rate at lower irradiation doses, but with higher doses, survival decreases precipitously. This means that repeated small doses will be ineffective against melanoma cells because of recovery between doses. Large doses will be more effective to these cells.

In the course of this experimental work, it became evident that these spheroids shed B-16 cells, making it necessary to re-evaluate whether the clonogenicity method as described above could still reflect inactivation of irradiated test cells. This question was approached in the following manner: two batches of HeLa feeder cells were mixed with a smaller number (1:25) of B-16 cells each, but in one case, this number consisted of one fourth viable B-16 cells, and three fourths of heavily irradiated B-16 cells. In the other case, only viable B-16 cells were used. After overnight incubation, spheroids of the desired size were collected and transferred into individual wells of 96 well tissue culture plates. Data listed in Table III show that with this method of plating (to prevent the loss of B-16 cells from the assigned area), the relationship between the live test and feeder cells in the initial suspensions is also maintained in the corresponding clonogenicities measured in the two hybrid spheroid populations. It was concluded therefore, that the hybrid spheroid method was also suitable for measuring survival in cells other than HeLa, even when shedding may reduce the numbers of test cells in spheroids before their plating.

While Table III shows that hybrid spheroids can be used to measure survival of irradiated B-16 cells, the utility of the system is presently restricted by two factors: 1) it is not practical to run entire survival curves (requiring at least 4 data points) with the individual manual placement of hybrid spheroids in 96 well plates, and 2) the problem of migrant test cells is intensified when hybrid spheroids with B-16 cells are plated in flasks. For these reasons, no attempt was made to correct for cell multiplicity, and in fact, it was found that excellent agreement between the two assay methods was obtained without this correction. However, in order to achieve an extension of the survival curve into lower survival values, an increased input of B-16 test cells into hybrid spheroids was used for larger irradiation doses, for which appropriate corrections were applied (FIGS. 3A-B). Therefore, it is evident that when these factors are taken into account, the B-16-HeLa hybrid spheroid curve ($D_0 = 1.40 \pm 0.06$ Gy, $n=5.9$ (4.0–8.7, 95% FL)) is not significantly different ($D_0$ $t_{60} = 1.061, 0.5 > p > 0.25$) from the free B-16 cell suspension survival curve ($D_0 = 1.31 \pm 0.06$ Gy, $n=7.7$ (4.7–12.7, 95% FL)). Included in the latter group are datapoints (triangles) pertaining to cells obtained from the dispersion of hybrid spheroids containing B-16 cells, showing that, save for the issues of cell shedding and multiplicity, all B-16 cells have similar radiosensitivities. Thus, survival curves can be obtained with hybrid spheroids, even when test cells are of a heterogenous type, and where adherence of these to HeLa feeder cells may be a problem.

EXAMPLE 2

To demonstrate further the validity of the hybrid spheroid method for clonogenicity measurements, it was tested in a system where it could be compared with the conventional clonogenicity assay method. Consequently, HeLa test:HeLa feeder cell hybrid spheroids were used to compare clonogenicity data with data obtained in the conventional manner. This example demonstrates that the survival curves of viable HeLa cells irradiated in spheroids are very similar to the survival curves of HeLa cells irradiated in suspension. The example also serves to illustrate the application of a cell multiplicity correction for those cases (e.g., test cells irradiated within spheroids), in which average clonogenicity is under-estimated using the standard poisson distribution function.

Clonogenicity of HeLa-HeLa Hybrid Spheroids

In order to obtain a population of hybrid spheroids in which only a fraction was capable of forming colonies, non-clonogenic HeLa feeder cells were co-agglomerated with viable HeLa cells capable of forming colonies. By a judicious combination of the two types of cells in the initial suspension, hybrid spheroids with a desired colony forming capacity were obtained. After an overnight incubation, cellular agglomerates of various sizes were obtained (the length of incubation, cell density and culture vessel type and size were optimized for best spheroid yield). These spherical agglomerates were passed through a series of nylon mesh sieves as previously described. A typical spheroid, which had passed through a 105 micrometer pore sieve, and was retained on a 88 um pore sieve, is shown in FIG. 1. Such spheroids, composed of HeLa feeder cells, contain on the average 107±9 (S.D.) cells.

Figure 4A:
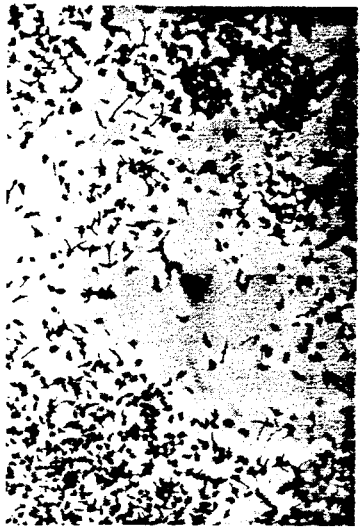
FIGS. 4A-D: Show encircled HeLa spheroids and their descendants. All four figures are shown at 30 times magnification.
Figure 4B:
Figure 4C:

To measure clonogenicity, hybrid spheroids harvested from the 88 micrometer pore sieve were plated in 30 ml tissue culture flasks at a density of about 150 per flask, where they were allowed to attach to the bottom of the flask. To be able to relate colonies formed to individual spheroids plated, the positions of the latter were marked in indelible ink on the outside of the flasks soon after attachment to the growth surface (usually within 1.5 hour). FIG. 4A shows the appearance of a spheroid, stained one hour after plating. FIG. 4B shows a colony formed (11 days later) from an encircled spheroid produced from a suspension of test and feeder cells, mixed in a 1 to 100 ratio; FIG. 4C shows remnants of another encircled spheroid, produced from the same cell suspension as the spheroid in FIG. 4B, but which had failed to produce a colony. In the entire flask, some circles are filled with well developed colonies, while other circles contain only an assembly of no more than 30 disfigured cells. The latter are identical in appearance to those obtained from spheroids composed entirely of feeder cells, and incubated over a period of time comparable to that needed for the formation of normal colonies. Several preparations of spheroids were examined in this fashion, and their clonogenicities calculated from the zero term of the poisson distribution of colony formers, as outlined in Example 1 and the specification. Table IV lists these values, and it can be seen that overall, a reasonable agreement exists between them and what one might expect from the input of test cells per spheroid of the selected size. A Chi-square test demonstrates a lack of significant difference between the expected and the actual ratios of test cells per spheroid ($X^2=0.0245$, $p>0.995$).

Survival of HeLa Cells Irradiated and Maintained in Hybrid Spheroids

Figure 4D:
Figure 4E:
Figure 4F:

In order to demonstrate that the survival of irradiated test HeLa cells can be measured by the clonogenicity method outlined above, hybrid spheroids were irradiated and their clonogenicity compared with that obtained in the conventional manner, by measuring the colony forming ability of cells from dispersed spheroids. In both instances the parameters measured were the same - the number of surviving clonogens per spheroid after a given dose of radiation. When such a procedure was performed with hybrid spheroids obtained from a mixed cell suspension composed of one test to ten feeder cells, and then irradiated with 5.5 Gy of x-rays, clonogenicities determined in whole and in dispersed spheroids were indistinguishable within experimental error (Table V). Here the situation is different than in unirradiate spheroids where clonogens were incorporated in some, but not in all spheroids. In irradiated spheroids, where initially all spheroids contained clonogens, it is the number of clonogens at the time of irradiation which is measured. Another distinction from unirradiated spheroids is that circles classified as non-colonies sometimes contain more than the assembly of cells remaining after spheroid disintegration; such groups of cells are always distinguishable from true colonies, even when containing more than 50 cells (FIG. 4D).

Using clonogenicity measurements for irradiated spheroids, absolute survival values could be obtained, provided that the corresponding value for the unirradiated series is known. This control value was obtained from the colony forming ability of cells dispersed from unirradiated spheroids, and together with the derived survival values for irradiated spheroids, is listed in Table V.

While a limited period of time in hybrid spheroids does not seem to affect survival of irradiated cells adversely, it remained to be shown that prolonged incubation of irradiated hybrid spheroids in a spherical form was achieved by incubation in soft agar. When embedded irradiated spheroids were released from soft agar and transferred into culture vessels with liquid medium, spheroids flattened, and those containing viable test cells formed colonies. Table VI shows the result of a test where irradiated spheroids were maintained for up to 6 days in soft agar. It can be seen that within experimental error, clonogenicity did not change with prolonged contact of cells in spheroids.

Survival Curves Obtained By Irradiating Spheroids With HeLa Test Cells

Survival values can also be obtained without dispersal of spheroids, irradiated or unirradiated. This was achieved by relating clonogenicities of irradiated spheroids to the clonogenicity of unirradiated spheroids, in a manner analogous to that obtained with the conventional plating method. However, the survival values obtained are for whole spheroids, not for individual cells comprising the hybrid spheroids. To obtain the survival values for individual cells, one has to correct the values obtained for whole spheroids, with the cell multiplicity factor. This factor reflects the increase in the number of clonogens per spheroid between the inception and the treatment of hybrid spheroids.

The procedure for correcting whole spheroid survival (obtained from relating clonogenicities of the treated and untreated series), to obtain single cell survival, is as follows:

$$S.F.(s.c.) = 1 - (1 - S.F.(spher.))^{1/M} \tag{5}$$

where S.F.(s.c.) is the surviving fraction of single cells, S.F.(spher.) is the surviving fraction of whole spheroids, and M is cellular multiplicity. The last value was obtained by trypsinizing a known number of spheroids and plating them for colony formation and noting the excess of clonogens so determined over that determined from the poisson distribution function.

Another correction pertains to the use of spheroids with a multiple input of test cells, intended for irradiation with higher doses. This correction factor is applied to clonogenicity values obtained from the ratios of non-colony-forming spheroids to the total numbers of spheroids scored, according to poisson statistics. In this fashion, spheroid survival can be extended beyond the limit imposed by the scoring ability of colonies formed from hybrid spheroids with a low input of test cells. Only after such spheroid survival is set, does one apply the cell multiplicity correction, to obtain the single cell survival curve.

An example of survival values obtained from clonogenicity measurements in irradiated and control hybrid spheroids, and the application of the two corrections, to obtain single-cell survival, is shown in Table VII. It can be seen that when the clonogenicity of irradiated 1:20 (test:feeder) spheroids is to be compared with the control 1:100 spheroids, the correction factor for the increased input of test cells in the former spheroids is (101:1)/(21:1) 4.8. Once normalized for the increased input of test cells, the 1:20 spheroids have the same S.F. as do the 1:100 spheroids (see Table VII, the range of 1:100 values include the 1:20 values). After survival values for spheroids were obtained, the cell multiplicity correction was applied as outlined above. These survival values, after the required corrections, were also used to construct the survival curve shown in FIG. 5A (inverted triangles).

FIG. 5A represents the composite survival curve of HeLa cells irradiated in hybrid spheroids, after the two corrections mentioned above, were introduced. In this and in subsequent survival curves, symbols for individual data points were entered (shaped differently for different experiments) to graphically demonstrate the spread obtained with both the hybrid spheroid and the conventional method. In FIG. 5B the conventionally obtained survival curve for surface-attached HeLa cells is presented, also after cell multiplicity corrections. Comparing FIGS. 5A and 5B, it can be seen that the survival curve of HeLa cells irradiated in spheroids ($D_0 = 1.10 \pm 0.05$ Gy, $n = 3.8$ (2.6–5.4 95% FL)) is similar to that for cells irradiated in monolayer ($D_0 = 1.33 \pm 0.03$ Gy, $n = 1.3$ (1.1–1.6, 95% FL)), but the small differences in $D°$ and n are statistically significant ($D_0 t_{99} = 3.944$, $p < 0.005$; $\ln(n) t_{99} = 5.122$, $p < 0.005$).

Figure 6A:
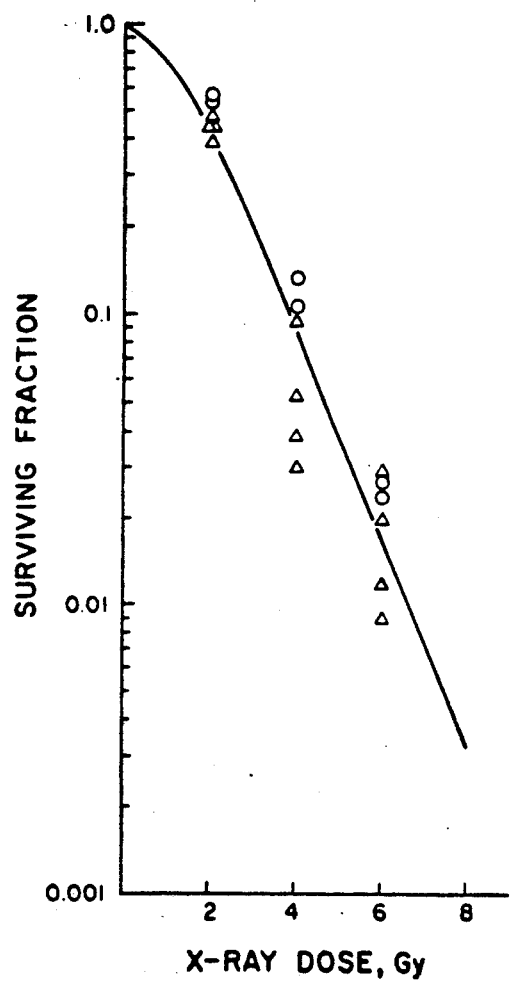
FIGS. 6A-B.
Figure 6B:
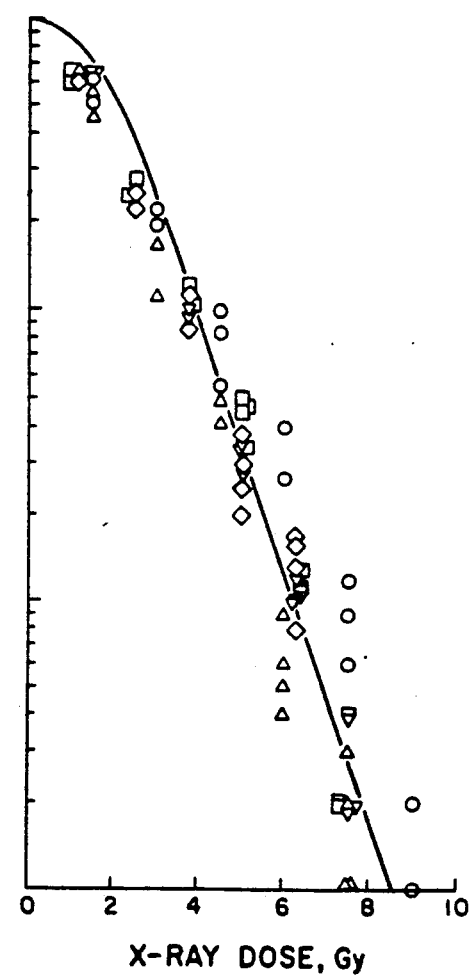

FIG. 6A pertains to HeLa test cells irradiated first and then incorporated into spheroids. FIG. 6B pertains to cells irradiated in suspension and then plated. Because irradiated cells were dispersed before incorporation into spheroids, no cell multiplicity corrections were necessary. The other correction (for increased input of test cells) was still used for hybrid spheroids where applicable, i.e., when different inputs of test cells into spheroids were used to compensate for increased cell killing by radiation. Comparing curves 6A and 6B, the survival curve parameters for HeLa cells irradiated in suspension and then incorporated into spheroids ($D_0 = 1.22 \pm 0.09$ Gy, $n = 2.3$ (1.4–3.8, 95% FL)) vs. those for cells similarly irradiated but then immediately plated into culture vessels ($D_0 = 0.99 \pm 0.04$ Gy, $n = 5.2$ (3.0–9.0, 95% FL)) are similar but the small differences in $D°$ and n values are statistically significant ($D_0 t_{67} = 2.335$, $0.01 < p < 0.025$; $\ln(n) t_{67} = 2.198$, $0.025 < p < 0.05$).

FIG. 6B also contains data points (inverted triangles) pertaining to HeLa cells irradiated after dispersal from hybrid spheroids. No significant difference in survival ($p > 0.5$) is observed relative to other data points (for the same radiation dose) in this Figure. Therefore the radiation responses are similar, whether cells had a previous sojourn in spheroids or not.

It should be emphasized that Example 2 is presented to show the similarity in survival obtained by the two methods in such a culture where both are applicable. In cases where dispersed cells are incapable of forming colonies, the spheroid method would be advantageous.

EXAMPLE 3

Figure 7A:
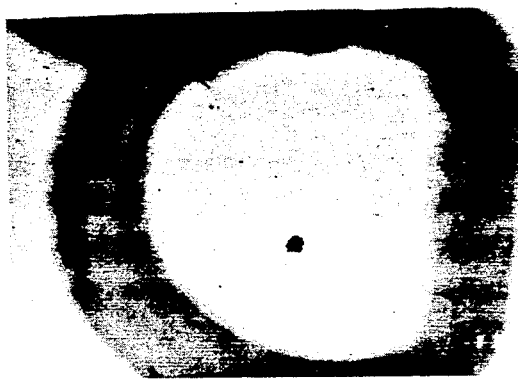
Figure 7B:
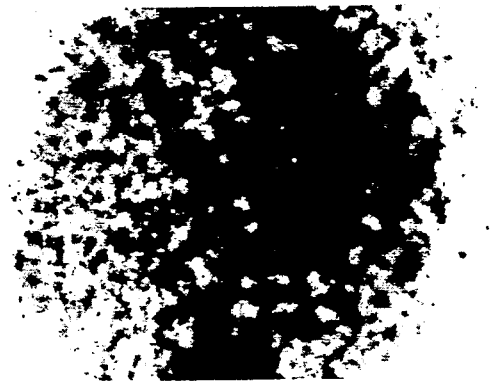
Figure 7C:
Figure 7D:
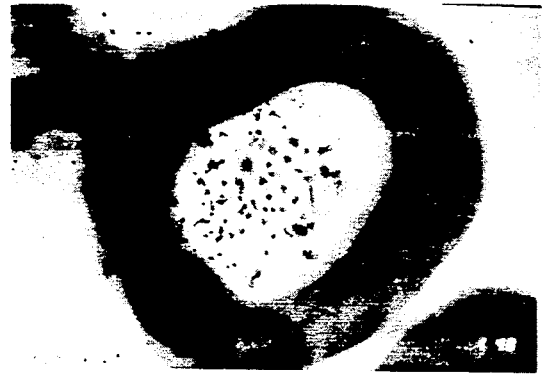

Survival Of Cells From Primary Lines And From Surgical Specimens, Irradiated In Hybrid Spheroids The ultimate test for the utility of the novel hybrid spheroid assay method is for it to prove advantageous over the conventional plating method. Such a situation may be seen with cultures with poor plating characteristics, where quantitation of colony forming ability may be assessed more easily with the former, than with the latter method. Based on Applicant's experience, there are cell cultures, such as the human epidermoid carcinoma line HEp3, which have a tendency to grow optimally only near confluence. In these cultures, plating at low density even in the presence of heavily irradiated HEP3 feeder cells, yields colony formers at a very low frequency. With a higher density of plating, the Applicant's work showed that efficiency improved, but difficulties were encountered in scoring true colonies amongst the background growth (FIG. 7A). When HEp3 cells were incorporated in hybrid spheroids, a more distinct grouping of cells was obtained (FIG. 7B). Moreover, the plating efficiency of HEp3 cells grown in hybrid spheroids was higher than for cells plated directly. This was deduced from the following considerations: since about 100 cells comprise a spheroid, 17 of which (on the average) are HEp3 cells in a 1:5 spheroid (100/(1+5) 16.7), and that clonogenicity for such spheroids is about 1.7 (see description for FIG. 8), a plating efficiency of about 10% was obtained. This should be compared with an estimated plating efficiency of about 2.5% for HEp3 cells plated directly (see description for FIGS. 7A-F). Thus a fourfold increase in colony forming ability was obtained with HEp3 cells growing in spheroids compared to cells plated directly and growing under optimal monolayer conditions. An even higher differential is obtained if cells are plated at a lower density. However, it must be remembered, that the terms "Plating Efficiency" and "Clonogenicity" are used here (for HEp3 cells) in an operational sense, since it is not known whether colonies descend from single progenitor cells or not, although poisson statistical considerations applied to these data suggest that they do. Nevertheless, it is clear that a better quantification was possible with the hybrid spheroid method, than with cells plated directly, even for the irradiated series (FIGS. 7D-F).

Figure 8:
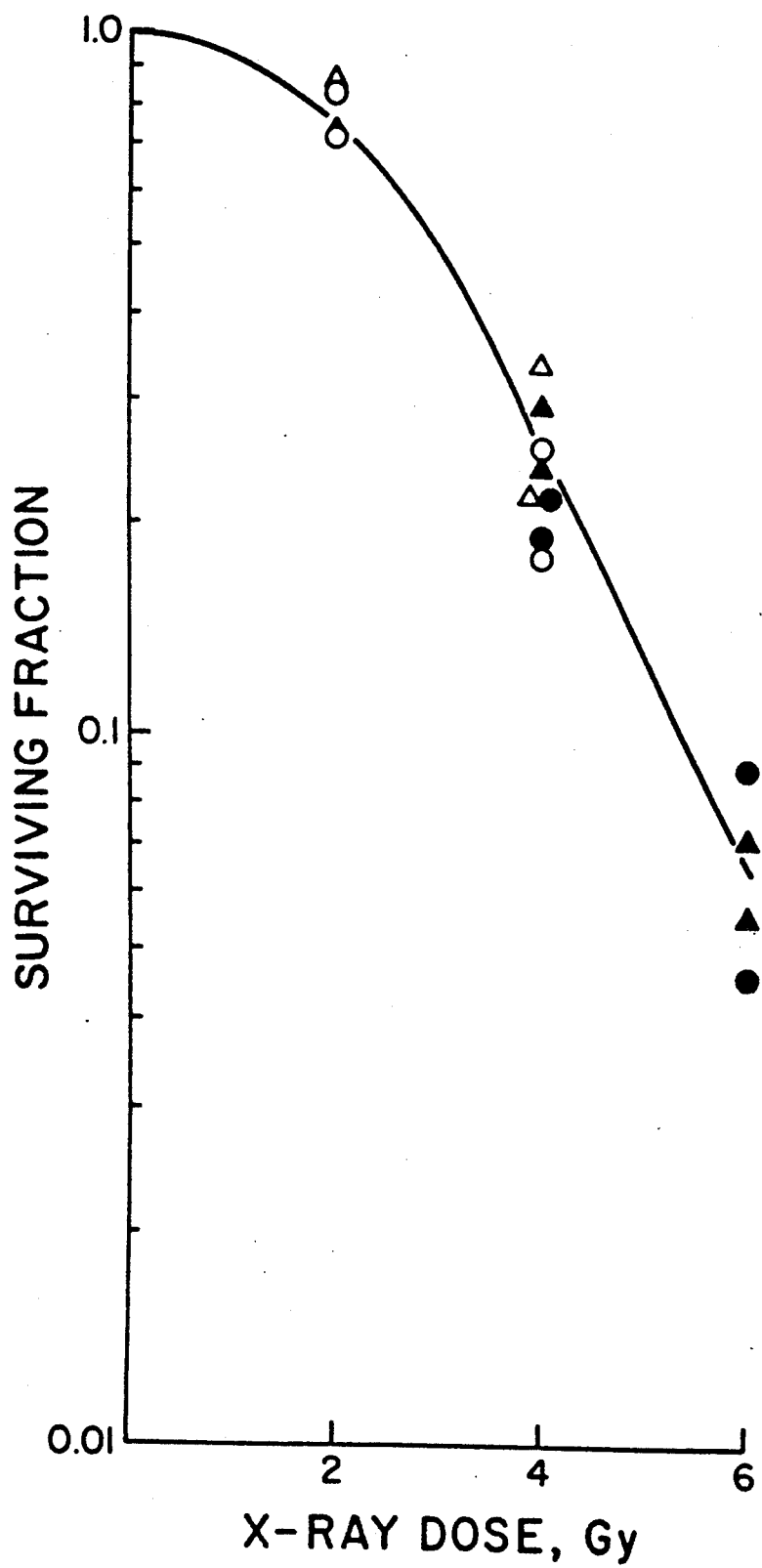
FIG. 8: Is a survival curve for HEp3 cells irradiated in spheroids. Circles denote spheroids irradiated 1.5 h after plating; triangles denote spheroids irradiated 20 h after plating. Open symbols represent 1:5 test to feeder cell hybrid spheroids; full symbols represent 1:1 hybrid spheroids. A correction factor of 5 was used for the full symbol series. Survival curve parameters for cells irradiated in spheroids are: $D_0=1.54\pm0.17$ Gy, n=3.2 (95% FL, 1.7–6.0).

In spite of the uncertainties of the nature of scored colonies (i.e., cooperative groups, vs. descendants of single cells), a survival curve was constructed from data obtained from HEp3 cells irradiated with 2, 4, and 6 Gy (FIG. 8). Included in the curve are data points for two different times of irradiation, and for spheroids with two different inputs of test cells. The clonogenicity data for the higher test cell input spheroids were adjusted for the purpose of survival measurement, by a factor of 5, permitting the best agreement of high input and low input test cell spheroid survivals. No corrections for cell multiplicity were made, since it was assumed from the similar survival profiles for the two irradiation times, that no proliferation had occurred in spheroids before irradiation.

Similar results were obtained when cells isolated directly from human tumor surgical specimens were used as test cells in hybrid spheroids. Here, because the colony forming ability of cells obtained from freshly dispersed tumors is generally not known, although assumed to be low, one prepares spheroids with a high input of test cells, and also uses in parallel series spheroids which are larger than the standard 100 micrometers. An experiment of this type is shown in Table VIII, where cells directly isolated from a human maxillar melanoma were used as test cells in a ratio of one to five feeder cells. It can be seen from Table VIII that clonogenicity in the resultant hybrid spheroids increases with their size, from 0.22 (mean of 0.19, 0.25, 0.21) per spheroid for the 100 micrometer standard spheroid, to 1.23 (mean of 1.12, 1.34) for the nominally 137 micrometer (125-149 micrometer) spheroids. Based on a plating efficiency of 0.04% for test cells plated directly at a density of $2.5 \times 10^4$ per 60 mm petri dish, and using a calculation similar to that used for HEP3 cells, roughly a 25 fold increase in Plating Efficiency (PE) was obtained due to a sojourn in the smallest spheroids used (PE 1.1%) and a ca. 60 fold increase for the largest spheroids (PE 2.5%). In spite of the apparent dependence of PE on spheroid size (marginally significant, $(0.10 > p > 0.05)$), survival values after 1.5 Gy were statistically indistinguishable among the spheroids of different sizes ($p > 0.5$) This finding clearly demonstrates the advantage of the hybrid spheroid method in assaying the clonogenicity of poorly plating cells.

Thus, the method disclosed herein for conducting clonogenicity studies comprising use of multicellular spheroids wherein the test cells are encased in feeder cells for clonogenicity studies provides an improved in vivo-like environment. The method is especially valuable when a three-dimensional cell-to-cell contact is desired or where cells that grow poorly when dissociated have to be tested. A particular important application of this Assay Method is for the determination of the sensitivity of individual tumors to various radiation and/or drug treatment procedures.

TABLE 1

Type and Organ of Origin of Human Tumor Cells Incorporated into Hybrid Spheroids by the Method of Example 1.

| DIAGNOSIS | ORGAN OF ORIGIN |
| --- | --- |
| 1. Metastatic Melanoma | Lung (Bronchus) |
| 2. Breast Cancer | Breast |
| 3. Metastatic Colon Cancer | Liver |
| 4. Metastatic Breast Cancer | Breast |
| 5. Metastatic Osteosarcoma | Lung |
| 6. Melanoma of Maxilla | Maxilla |
| 7. Metastatic Colon Cancer | Liver |
| 8. Adenocarcinoma | Esophagus |
| 9. Breast Cancer | Breast |
| 10. Gastric Cancer | Stomach |
| 11. Groin Melanoma | Groin |
| 12. Metastatic Adrenal Carcinoma | Adrenal Gland |

TABLE II

Survival Value Calculations (Data For FIG. 2)

| Rad. (Dose, Gy) | Exp. No. | Test: feeder cells in susp. | Colonies Formed/ Spheroids Plated | Clonogens/ Spheroid$^a$ | Fractional$^b$ Survival |
| --- | --- | --- | --- | --- | --- |
| 0 | 123 | 1:100 | 8/24 | 0.41 | |
| 0 | 123 | 1:100 | 32/96 | 0.41 | |
| 0 | 125 | 1:40 | 73/96 | 0/58$^c$ | |
| 0 | 131 | 1:100 | 5/20 | 0.29 | |
| 0 | 136 | 1:100 | 28/94 | 0.35 | |
| 0 | 138 | 1:57 | 12/24 | 0.40$^c$ | |
| | | | | Mean $0.43 \pm 0.09^d$ | |
| 2.5 | 130 | 1:20 | 75/96 | 1.52 | $0.734 \pm 0.153^d$ |
| 2.5 | 130 | 1:40 | 13/24 | 0.78 | $0.736 \pm 0.154$ |
| 5.0 | 128 | 1:10 | 58/77 | 1.40 | $0.354 \pm 0.074$ |
| 8.0 | 127 | 1:10 | 50/96 | 0.73 | $0.186 \pm 0.039$ |
| 8.0 | 132 | 1:10 | 13/96 | 0.14 | $0.037 \pm 0.008$ |
| 8.5 | 134 | 1:6.9 | 34/96 | 0.44 | $0.080 \pm 0.016$ |
| 9.0 | 129 | 1:5 | 17/96 | 0.19 | $0.027 \pm 0.006$ |
| 9.0 | 132 | 1:10 | 9/96 | 0.10 | $0.013 \pm 0.003$ |
| 9.0 | 134 | 1:5.7 | 33/96 | 0.42 | $0.065 \pm 0.014$ |

$^a$Obtained from: - ln (1-(colonies formed/spheroids plated)).
$^b$From equation (4), using the mean of clonogens per spheroid in unirradiated series (normalized to 1:100 test to feeder cell spheroids) + 0.43 ± 0.09, in denominator.
$^c$Normalized to 1:100 spheroids.
$^d$Standard deviation of the weighted mean.

TABLE III

Colony Forming Ability of Hybrid Spheroids Containing Various Proportions of Viable B-16 Cells.

| Initial Cell Suspension | | Colonies/ Spheroids | Clonogens/ Spheroid | Clonogenicity Changes | |
| --- | --- | --- | --- | --- | --- |
| Total B-16: HeLa Feeder | Viable B-16: HeLa Feeder | | | Predicted | Observed |
| 1:25 | 1:100 | 19/88 | 0.216$^a$ | 4.0$^b$ | 4.4$^c$ |
| 1:25 | 1:25 | 66/107 | 0.959 | | |

$^a$From Eq 2.
$^b$From (1/25)/(1/100) = 4.0. This differs from the multiplicity correction shown in Table VII note d because the number of B-16 cells remains constant, only the viable fraction is changed.
$^c$From 0.959/0.216 = 4.4

TABLE IV

Clonogenicity of HeLa-HeLa Hybrid Spheroids

| Test cells: feeder cells | Circles with colonies | Empty Circles | Clonogens/ spher. (calc)$^a$ | Clonogens/ spher. (expect)$^b$ |
| --- | --- | --- | --- | --- |
| 1:100 | 53 | 28 | 1.06 | 1.06 |
| 1:100 | 74 | 39 | 1.06 | 1.06 |
| 1:100 | 81 | 45 | 1.03 | 1.06 |
| 1:100 | 68 | 43 | 0.95 | 1.06 |
| 1:100 | 19 | 12 | 0.95 | 1.06 |
| 1:100 | 45 | 25 | 1.03 | 1.06 |
| 1:33 | 49 | 5 | 2.38 | 3.15 |
| 1:33 | 67 | 4 | 2.88 | 3.15 |

$^a$Obtained from Eq. 2.
$^b$Calculated on the basis of 107 ± 9 cells per spheroid divided by 101 (100 + 1, first 6 cases), or 34 (33 ± 1, last 2 cases). S.D. 1:100 = ±0.09, 1:33 = ±0.27.

TABLE V

Clonogenicity and Survival of Irradiated Hybrid Spheroids[a]

Undispersed Spheroids

| Circles with colonies | Empty circles | Clonogens/ spheroid | Surviving fraction[b] |
|---|---|---|---|
| 48 | 27 | 1.02 | 0.051 |
| 28 | 26 | 0.73 | 0.036 |
| 51 | 57 | 0.64 | 0.032 |
|  |  |  | 0.040 ± 0.01[c] |

Dispersed Spheroids

| Total spheroids scored in dish | Total number of colonies counted[d] | Clonogens/ spheroid | Surviving fraction[b] |
|---|---|---|---|
| 146 | 137 | 0.94 | 0.047 |
| 92 | 97 | 1.03 | 0.051 |
| 159 | 143 | 0.90 | 0.045 |
|  |  |  | 0.048 ± 0.003[c] |

[a]1:10 HeLa-HeLa spheroids irradiated with 5.5 Gy 20 hours after mixing test and feeder cell suspensions.
[b]Calculated on the basis of 20 clonogens per unirradiated spheroids, at the time of irradiation, obtained by dispersal.
[c]Standard deviation of the sample mean.
[d]Obtained by plating dispersed spheroids.

TABLE VI

Effect of Holding Irradiated Hybrid Spheroids[a] in Soft Agar on Subsequent Colony Forming Ability[b]

|  | No holding |  | 30 min |  | 1 day |  | 2 days |  | 3 days |  | 6 days |  |
|---|---|---|---|---|---|---|---|---|---|---|---|---|
| Flask # | #1 | #2 | #1 | #2 | #1 | #2 | #1 | #2 | #1 | #2 | #1 | #2 |
| Spheroids scored | 60 | 93 | 82 | 73 | 80 | 74 | 84 | 101 | 97 | 112 | 125 | 89 |
| Spheroids w/colonies | 57 | 83 | 73 | 71 | 70 | 66 | 79 | 95 | 93 | 103 | 110 | 79 |
| Clonogens/ spheroids[c] | 3.0 | 2.2 | 2.2 | 3.6 | 2.1 | 2.2 | 2.8 | 2.8 | 3.2 | 2.5 | 2.1 | 2.2 |

Clonogens per spheroid, Mean ± S.D. = 2.6 ± 0.5
[a]Spheroids obtained from a suspension with 1 test to 10 feeder HeLa cells and irradiated with 4 Gy after plating in liquid medium or soft agar.
[b]Colonies scored after transfer from soft agar into flasks with liquid medium.
[c]Obtained from eq. 2.

TABLE VII

Survival of Irradiated Hybrid Spheroids[a]

| Rad dose [Gy] | Test cells: feeder cells[d] | Circles with colonies | Empty circles | Clonogens/ spheroid | S.F.[b] | S[c] |
|---|---|---|---|---|---|---|
| 0 | 1:100 | 45 | 25 | 1.03 | 1.00 | 1.00 |
| 0 | 1:100 | 19 | 12 | 0.95 |  |  |
| 3.75 | 1:100 | 16 | 90 | 0.16 | 0.16 | 0.11 |
| 3.75 | 1:100 | 18 | 63 | 0.25 | 0.25 | 0.17 |
| 3.75 | 1:20 | 63 | 47 | 0.85 | 0.18 | 0.12 |
| 3.75 | 1:20 | 71 | 54 | 0.84 | 0.18 | 0.12 |

[a]Example calculation of some of the data points entered in FIG. 3A as inverted triangles.
[b]S.F. = surviving fraction of whole spheroids (S.F.$_{(spher)}$ in eq. 5).
[c]S = surviving fraction of clonogens (S.F.$_{(cell)}$ in eq. 5) based on a multiplicity factor of 1.57.
[d]For the 1:20 ratio, the correction factor used to normalize the clonogenicity for the increased input of test cells in 4.8, from $(1/20 + 1))/(1/(100 + 1))$.

TABLE VIII

Survival Value Calculations for Human Maxillar Melonoma Cells Irradiated in Spheroids

| Spheroid, size, μm[a] | Radiation dose, Gy | Circles with Colonies | Empty Circles | Clonogens/ Spheroid[b] | Fractional Survival[c] |
|---|---|---|---|---|---|
| 125-149 | 0 | 58 | 28 | 1.12 | 1.00 ± 0.18 |
|  |  | 82 | 29 | 1.34 |  |
|  | 1.5 | 43 | 74 | 0.46 | 0.36 ± 0.05 |
|  |  | 44 | 84 | 0.42 |  |
| 105-125 | 0 | 39 | 43 | 0.65 | 1.00 ± 0.11 |
|  |  | 42 | 53 | 0.58 |  |
|  | 1.5 | 23 | 70 | 0.28 | 0.38 ± 0.11 |
|  |  | 17 | 82 | 0.19 |  |
| 88-105 | 0 | 20 | 97 | 0.19 | 1.00 ± 0.20 |
|  |  | 15 | 53 | 0.25 |  |
|  |  | 25 | 106 | 0.21 |  |
|  | 1.5 | 7 | 107 | 0.063 | 0.30 ± 0.07 |
|  |  | 8 | 97 | 0.079 |  |
|  |  | 6 | 108 | 0.054 |  |

[a]Spheroids passed through larger-pore sieve, harvested from smaller pore sieve.
[b]Obtained from: -ln (1 - (colonies formed/spheroids plated)).
[c]Mean ± standard error of the sample, without cellular multiplicity corrections. N.B. the SEM of all points includes the uncertainty of the denominator (zero dose clonogens/spheroid).

What is claimed is:

1. A method for forming clonable hybrid multicellular spheroids comprising the steps of:
   (a) providing nonproliferating, metabolically active feeder cells capable of forming spheroids;
   (b) providing test cells incapable of forming spheroids alone;
   (c) combining the feeder cells and the test cells in a ratio of approximately 1:5 to 1:100 test cells to feeder cells;
   (d) allowing the feeder cells and the test cells to contact each other such that clonable hybrid spheroids are formed containing feeder cell sand entrapped test cells; and
   (e) harvesting the hybrid spheroids.

2. The method of claim 1 wherein feeder cells are rendered capable of agglomerating by treating with inactivated virus, ethylene glycol or "Minimal Essential Medium" (MEM) supplemented with fetal calf serum.

3. The method of claim 2 wherein feeder cells are rendered capable of agglomerating by treating with "Minimal Essential Medium" (MEM) supplemented with fetal calf serum.

4. The method of claim 1 wherein feeder cells are rendered non-proliferating but metabolically active by subjecting said feeder cells to chemical, physical, including radiation, treatments or a combination thereof.

5. The method of claim 4 wherein the feeder cells are rendered non-proliferating by incubating for 3 days in the presence of $2 \times 10^{-5}$ M bomodeoxyuridine and $1.5 \times 10^{-8}$ M flurodeoxyuridine followed by irradiation with X-rays of 10 Gy.

6. The method of claim 4 wherein the feeder cells are rendered non-proliferating by illumination with a 15 watt fluorescent lamp for about 20 minutes.

7. The method of claim 4 wherein the feeder cells are rendered non-proliferating by incubation with bromodeoxyuridine and flurodeoxyuridine followed by X-irradiation or illumination with fluorescent light.

8. The method of claim 7 wherein the feeder cells are incubated from 1 to 3 days with from about $10^{-6}$ M to $10^{-4}$ M bromodeoxyuridine and from about $10^{-10}$ M to $10^{-7}$ M flurodeoxyuridine.

9. The method of claim 8 wherein the feeder cells are incubated for 3 days with $2\times10^{-5}$ M bromodeoxyuridine and $1.5\times10^{-8}$ M flurodeoxyuridine.

10. The method of claim 8 wherein the feeder cells are rendered non-proliferating by irradiation with X-rays at doses of from about 7.5 Gy to 30 Gy.

11. The method of claim 10 wherein the feeder cells are irradiated with an X-ray dose of 10 Gy.

12. The method of claim 1 wherein the test cells are encased in said non-proliferating but metabolically active feeder cells by:
(a) forming a suspension of said feeder cells;
(b) adding the test cells; and
(c) incubating the resulting suspension from about 8 to about 20 hours.

13. The method of claim 12 wherein in step (c), the feeder and test cell suspension is incubated about ten hours at about 37° C. in a 5% $CO_2$ incubator.

14. The method of claim 12 wherein the resulting hybrid multicellular spheroids are from about 85 to about 170 micrometers in diameter.

15. The method of claim 12 comprising the additional step of harvesting the resulting hybrid multicellular spheroids by passing the suspension containing said spheroids through a series of micrometer pore filters ranging from 88-149 micrometers and harvesting the spheroids retained on the next smaller size micrometer pore filter.

16. The method of claim 12 comprising the additional step of harvesting the resulting hybrid multicellular spheroids by passing the suspension containing said spheroids through a 105 micrometer pore filter and harvesting the spheroids retained on an 88 micrometer pore filter.

17. The method of claim 12 wherein incubation is conducted in the presence of Minimal Essential Medium.

18. The method of claim 12 wherein, prior to incubation, the combined feeder and test cell suspension is first centrifuged.

19. The method of claim 1 wherein the feeder cells are selected from the group consisting of HeLa and V79 Chinese hamster cells.

20. The method of claim 19 wherein the feeder cells are HeLa-S3 cells.

21. The method of claim 19 wherein the feeder cells are HeLa S-3 SKI cells.

22. An assay method for determining the clonogenicity of test cells incapable of forming spheroids alone comprising the steps of:
(a) subjecting the test cells to a treatment selected from the group consisting of heat, radiation, chemical treatments and combinations thereof;
(b) preparing clonable hybrid multicellular spheroids according to the method of claim 1, entrapping the treated test cells, such that only a fraction of the spheroids form colonies;
(c) determining the average number of clonogens per spheroid by assuming a random distribution of test cells among spheroids and solving for the zero-term of the Poisson distribution;
(d) determining survival of the test cells by comparing the average number of clonogens per spheroids obtained in step (c) to the average number of clonogens per spheroid in spheroids containing entrapped untreated test cells.

23. An assay method for determining the clonogenicity of test cells incapable of forming spheroids alone comprising the steps of:
(a) preparing clonable hybrid multicellular spheroids according to the method of claim 1 such that only a fraction of the spheroids form colonies;
(b) determining the average number of clonogens per spheroid by assuming a random distribution of test cells among spheroids and solving for the zero-term of the poisson distribution;
(c) subjecting the spheroids to a treatment selected from the group consisting of heat, radiation, chemical treatments and combination thereof; and
(d) determining survival of the test cells by comparing the average number of clonogens per spheroid after treatment to the average number of clonogens per spheroid before treatment.

24. A method according to claim 23 further comprising the step of correcting for a cell multiplicity factor in determining survival.

25. The method of claim 22 or 23 wherein said multicellular spheroids are subjected to treatment with a chemotherapeutic agent.

26. The method of claim 25, wherein the chemotherapeutic agent is selected from the group consisting of Adriamycin, doxorubicin hydrochloride, cyclophosphamide, cis-platinum, 5-fluorouracil, methotrexate, vinblastine sulfate, melphalan and vincristine sulfate.

27. A method according to claim 22 or 23 wherein the test cells are obtained directly from a mammalian tumor.

28. A method according to claims 22 or 23 wherein said hybrid multicellular spheroids are subjected to treatment with radiation or drugs.

29. Clonable hybrid multicellular spheroids comprising clonogenic test cells incapable of forming spheroids alone and nonproliferating, metabolically active feeder cells capable of forming spheroids in a proportion of approximately 0.10 to 3.00 clonogenic test cells per spheroid.

30. The clonable hybrid multicellular spheroids of claim 29 wherein the feeder cells are HeLa cells or V79 cells and the test cells are human tumor cells.

31. The clonable hybrid multicellular spheroids of claim 30 wherein the tumor cells are obtained directly from a mammalian tumor.

* * * * *